(12) United States Patent
Qin et al.

(10) Patent No.: US 10,525,173 B2
(45) Date of Patent: Jan. 7, 2020

(54) HYBRID IMPLANT SYSTEM AND MANUFACTURING METHOD THEREFOR

(71) Applicant: The Chinese University of Hong Kong, Hong Kong (CN)

(72) Inventors: Ling Qin, Hong Kong (CN); Yuk Sun Cheng, Hong Kong (CN); Ning Tang, Shati (CN); Wing Ho Chau, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 51 days.

(21) Appl. No.: 15/874,532

(22) Filed: Jan. 18, 2018

(65) Prior Publication Data

US 2018/0207327 A1      Jul. 26, 2018

(30) Foreign Application Priority Data

Jan. 18, 2017   (CN) .......................... 2017 1 0033338

(51) Int. Cl.
*A61L 31/14*      (2006.01)
*A61B 17/72*      (2006.01)
(Continued)

(52) U.S. Cl.
CPC ........ *A61L 31/148* (2013.01); *A61B 17/7233* (2013.01); *A61B 17/80* (2013.01);
(Continued)

(58) Field of Classification Search
CPC .. A61L 31/148; A61L 31/022; A61L 2430/02; A61B 17/7061; A61B 17/7233;
(Continued)

(56) References Cited

U.S. PATENT DOCUMENTS

| 6,808,527 B2 * | 10/2004 | Lower ................... A61B 17/72 606/62 |
| 2002/0128654 A1 * | 9/2002 | Steger ................ A61B 17/8047 606/291 |

(Continued)

FOREIGN PATENT DOCUMENTS

| CN | 101283992 | 10/2008 |
| CN | 101690676 | 3/2011 |

OTHER PUBLICATIONS

Windhagen et al.; "Biodegradable magnesium-based screw clinically equivalent to titanium screw in hallux valgus surgery: short term results of the first prospective, randomized, controlled clinical pilot study"; BioMedical Engineering online 2013; 12:62.

(Continued)

*Primary Examiner* — Pedro Philogene
*Assistant Examiner* — David C Comstock
(74) *Attorney, Agent, or Firm* — Fish & Richardson P.C.

(57) ABSTRACT

The present disclosure discloses a hybrid implant system for fixing and repairing orthopedic fracture and a manufacturing method therefor. The hybrid implant system comprises an implant body having holes on both ends and a locking part configured for attaching the implant body to a broken bone through the holes. The hybrid implant system further comprises a healing assembly made from a material promoting healing of the bone. The implant body has at least one window on a side, the at least one window is aligned with a broken location of the bone, and the healing assembly is inserted into the window in a self-locking manner towards an interior of the implant body.

16 Claims, 8 Drawing Sheets

(51) Int. Cl.
*A61B 17/80* (2006.01)
*A61L 31/02* (2006.01)
*A61B 17/00* (2006.01)

(52) U.S. Cl.
CPC ... *A61L 31/022* (2013.01); *A61B 2017/00526* (2013.01); *A61B 2017/00893* (2013.01); *A61L 2430/02* (2013.01)

(58) Field of Classification Search
CPC .......... A61B 17/80; A61B 2017/00526; A61B 2017/00893
USPC .................. 606/62, 280, 70, 71, 298, 76, 77
See application file for complete search history.

(56) References Cited

U.S. PATENT DOCUMENTS

| | | | | |
|---|---|---|---|---|
| 2002/0151898 | A1* | 10/2002 | Sohngen | A61B 17/68 606/62 |
| 2006/0093646 | A1 | 5/2006 | Cima et al. | |
| 2007/0016163 | A1 | 1/2007 | Santini, Jr. et al. | |
| 2007/0233115 | A1* | 10/2007 | Sixto | A61B 17/80 606/281 |
| 2008/0255558 | A1* | 10/2008 | Schlienger | A61B 17/72 606/62 |
| 2011/0192500 | A1* | 8/2011 | Uggowitzer | A61L 27/047 148/406 |
| 2014/0050942 | A1* | 2/2014 | Guo | A61L 27/58 428/687 |
| 2014/0243911 | A1* | 8/2014 | Almarza | A61B 17/8605 606/305 |
| 2014/0261911 | A1* | 9/2014 | Imwinkelried | C22C 23/04 148/557 |
| 2017/0044645 | A1* | 2/2017 | Kumta | C22C 23/06 |
| 2017/0095590 | A1* | 4/2017 | Manuel | A61L 31/022 |
| 2018/0093012 | A1* | 4/2018 | Ishikawa | A61B 17/744 |

OTHER PUBLICATIONS

Plass et al.; Bioabsorbable magnesium versus standard titanium compression screws for fixation of distal metatarsal osteotomies—3 year results of a randomized clinical trial; Journal of Orthopaedic Science; 2017; pp. 1-7.

Lee et al.; "Long-term clinical study and multiscale analysis of in vivo biodegradation mechanism of Mg alloy"; PNAS; Jan. 19, 2016, vol. 113, No. 3; pp. 716-721.
Zhao et al.; "Vascularized bone grafting fixed by biodegradable magnesium screw for treating osteonecrosis of the femoral head"; Biomaterials 81; 2016; pp. 84-92.
Zhang et al.; "Implant-derived magnesium induces local neuronal production of CGRP to improve bone-fracture healing in rats"; Nature Medicine, vol. 22, No. 10, Oct. 2016; 13 pages.
Holmes; "Neuronal origin of osteogenic effects of magnesium"; Nature Reviews Endocrinology; Sep. 16, 2016; 1 page.
Chen; "Magnesium-based implants: Beyond fixators"; Journal of Orthopaedic Translation, 2017, 10, pp. 1-4.
Tang et al.; "Surface coating reduces degradation rate of magnesium alloy developed for orthopaedic applications"; Journal of Orthopaedic Translation; 2013, 1, pp. 41-48.
Li et al.; "In vitro and in vivo studies on biodegradable CaMgZnSrYb high-entropy bulk metallic glass"; Acta Biomaterialia 9, 2013; pp. 8561-8573.
Li et al.; "Development of biodegradable Zn-1X binary alloys with nutrient alloying elements Mg, Ca and Sr"; Scientific Reports; May 29, 2015; 14 pages.
Ma et al.; "Bacterial inhibition potential of 3D rapid-prototyped magnesium-based porous composite scaffolds—an in vitro efficacy study"; Scientific Reports; Sep. 8, 2014; 14 pages.
Wang et al.; "Recommendation for modifying current cytotoxicity testing standards for biodegradable magnesium-based materials"; Acta Biomaterialia; 21; 2015; pp. 237-249.
Fan et al.; "Targeting cellular senescence prevents age-related bone loss in mice"; Nature Medicine; vol. 23, No. 9; Sep. 2017; 16 pages.
Ambrosi et al.; "Adipocyte Accumulation in the Bone Marrow during Obesity and Aging Impairs Stem Cell-Based Hematopoietic and Bone Regeneration"; Cell Stem 20, Jun. 1, 2017; pp. 771-784.
Zhai et al.; "The effect of metallic magnesium degradation products on osteoclast-induced osteolysis and attenuation of NF-kB and NFATc1 signaling"; Biomaterials 35, 2014; pp. 6299-6310.
Voor et al.; "Fatigue Properties of a Twelve-Hole Versus a Five-Hole Intramedullary Supracondylar Nail"; Journal of Orthopaedic Trauma; vol. 11(2); Feb./Mar. 1997; pp. 98-102.
Gu et al.; "In vitro and in vivo studies on a Mg—Sr binary alloy system developed as a new kind of biodegradable metal"; Acta Biomaterialia 8, 2012; pp. 2360-2374.
Zhao et al.; "Current status on clinical applications of magnesium-based orthopedic implants: A review from clinical translational perspective;" Biomaterials 112; 2017; pp. 287-302.

* cited by examiner

HYBRID IMPLANT SYSTEM AND MANUFACTURING METHOD THEREFOR

CROSS-REFERENCE TO RELATED APPLICATION

This application claims priority to Chinese Patent Application Serial No. 201710033338.0, filed on Jan. 18, 2017, the entire contents of which are herein incorporated by reference.

TECHNICAL FIELD

The present disclosure generally relates to the field of medical appliance, in particular to the technical field of orthopedic fixation device.

BACKGROUND

In recent years, noticeably increased trauma-related, sports-related and age-related musculoskeletal injuries have imposed significant medical and socioeconomic burden on patients, families and society.

Conventional orthopedic implants are made from permanent and rigid metals such as stainless steel or titanium (Ti). However, such metals do not have the function of promoting the healing of a broken bone. In addition, permanent metals usually create a stress shielding phenomenon, namely causing bone loss due to the decreased load to the fracture bone, thus impairing the healing, in particular unfavorable to the healing and fixation of an osteoporotic fracture.

Therefore, a material promoting healing through its biodegradability is very much desired clinically. Such material comprises a metal that may gradually degrade in vivo, and induces a proper host response by a released degradation product so as to assist the tissue healing. Such implants, besides efficacious, will be more cost-effective as their use may avoid implant removal surgery and/or related complications, including reducing the risks of re-fracture and infections.

Implants, such as intramedullary nail (IM nail), have long been used for long bone fracture fixation. The conventional implant is a metallic implant which is introduced into a medullary cavity of a bone such as femur, tibia and humerus to stabilize the fracture fragments and restore the anatomical location. In addition, an implant system is also responsible for sharing load and allowing early function of a injured limb. As the implant system is a load-sharing implant, certain stiffness and strength are desired. Therefore, conventional implant systems are made from stainless steel or titanium alloys which are permanent and rigid metals and strong enough to provide mechanical support. It is well known that a biodegradable material degrades over time, and the dimensions and mechanical strength thereof reduce, resulting in an unpredictable fracture fixing effect. Therefore, the biodegradable material may not be suitable for directly manufacturing an orthopedic fixing device for fixation of load-bearing skeletal sites where mechanical loading is imposed to the fixation implant or device.

SUMMARY

With regard to at least one of the shortcomings above in the prior art, the present disclosure provides a hybrid system treating various long bone fractures and having an enhanced healing effect and a manufacturing method therefor.

In one aspect, the present disclosure provides a hybrid implant system for fixing and repairing orthopedic fracture. The hybrid implant system may comprise an implant body and a locking part. The implant body may have holes on both ends thereof and the locking part may be configured for attaching the implant body to a broken bone through the holes. The hybrid implant system may further comprise a healing assembly. The healing assembly is made from a material promoting healing of the bone. The implant body may have at least one window on the side, the at least one window may be aligned with a broken location of the bone, and the healing assembly may be inserted into the window in a self-locking manner towards an interior of the implant body.

According to an implementation of the present disclosure, the healing assembly in the hybrid implant system may be made from biodegradable magnesium or magnesium alloys.

According to an implementation of the present disclosure, the healing assembly may have a resilient groove, the healing assembly may be inserted into the window towards the interior of the implant body, and the healing assembly may be snapped into the window by compressing the resilient groove.

According to an implementation of the present disclosure, the window in the implant body may comprise a first section and a second section on the side of the body in a direction from an outside to the inside, the first section having a inner diameter larger than a diameter of the second section. The healing assembly comprises a first holding section having a shape corresponding to the first section and a second holding section having a shape corresponding to the second section, wherein the resilient groove may be disposed in the second holding section.

According to an implementation of the present disclosure, the healing assembly in the hybrid implant system may gradually degrade during implantation.

According to an implementation of the present disclosure, the implant body in the hybrid implant system may be used for insertion into a broken bone.

According to an implementation of the present disclosure, the implant body may be a hollow rod with a hollow cavity, and the healing assembly may fall into the hollow cavity of the hollow rod only after falling off due to degradation.

According to an implementation of the present disclosure, the implant body in the hybrid implant system may be attached to an outer side of the broken bone.

According to an implementation of the present disclosure, the implant body in the hybrid implant system may have a plate shape.

In another aspect, the present disclosure provides a method for manufacturing a hybrid implant system for fixing and repairing orthopedic fracture. The method may comprise the following steps: forming holes on both ends of an implant body to attach the implant body to a broken bone through the holes; forming at least one window on a side of the implant body; manufacturing a healing assembly body with a material promoting healing of the bone; and forming a self-locking part in the healing assembly body. The at least one window may be aligned with a broken location of the bone, and the healing assembly may be inserted into the window in a self-locking manner through the self-locking part.

According to an implementation of the present disclosure, the healing assembly in the method for manufacturing a hybrid implant system may be made from biodegradable magnesium or magnesium alloys.

According to an implementation of the present disclosure, the self-locking part in the method for manufacturing a hybrid implant system may have a resilient groove. The healing assembly may be inserted into the window towards the interior of the implant body, and the healing assembly may be snapped into the window by compressing the resilient groove.

According to an implementation of the present disclosure, in the method for manufacturing a hybrid implant system, the forming at least one window on a side of the implant body may comprise: allowing the window to forma first section and a second section on the side of the body in a direction from an outside to the inside, the first section having a inner diameter larger than a diameter of the second section. The healing assembly body manufactured with a material promoting healing of the bone may comprise: a first holding section having a shape corresponding to the first section; and a second holding section having a shape corresponding to the second section. The resilient groove may be disposed in the second holding section.

According to an implementation of the present disclosure, the healing assembly in the method for manufacturing a hybrid implant system (e.g. magnesium or magnesium alloys) may gradually degrade during implantation.

According to an implementation of the present disclosure, the implant body in the method for manufacturing a hybrid implant system may be a hollow rod with a hollow cavity, and the magnesium or magnesium alloys as healing assembly may either fully degraded in place or fall into the hollow rod only after falling off due to degradation.

According to an implementation of the present disclosure, the implant body in the method for manufacturing a hybrid implant system may be used for insertion into a broken bone.

According to an implementation of the present disclosure, the implant body in the method for manufacturing a hybrid implant system may be attached to an outer side of the broken bone.

According to an implementation of the present disclosure, the implant body in the method for manufacturing a hybrid implant system may have a plate shape.

BRIEF DESCRIPTION OF THE DRAWINGS

Other features, objects and beneficial effects of the present disclosure will be apparent by reading the following detailed descriptions referring to the drawings. Same or similar elements in different drawings are indicated by same reference signs. In the attached drawings.

DETAILED DESCRIPTION OF EMBODIMENTS

Figure 1:
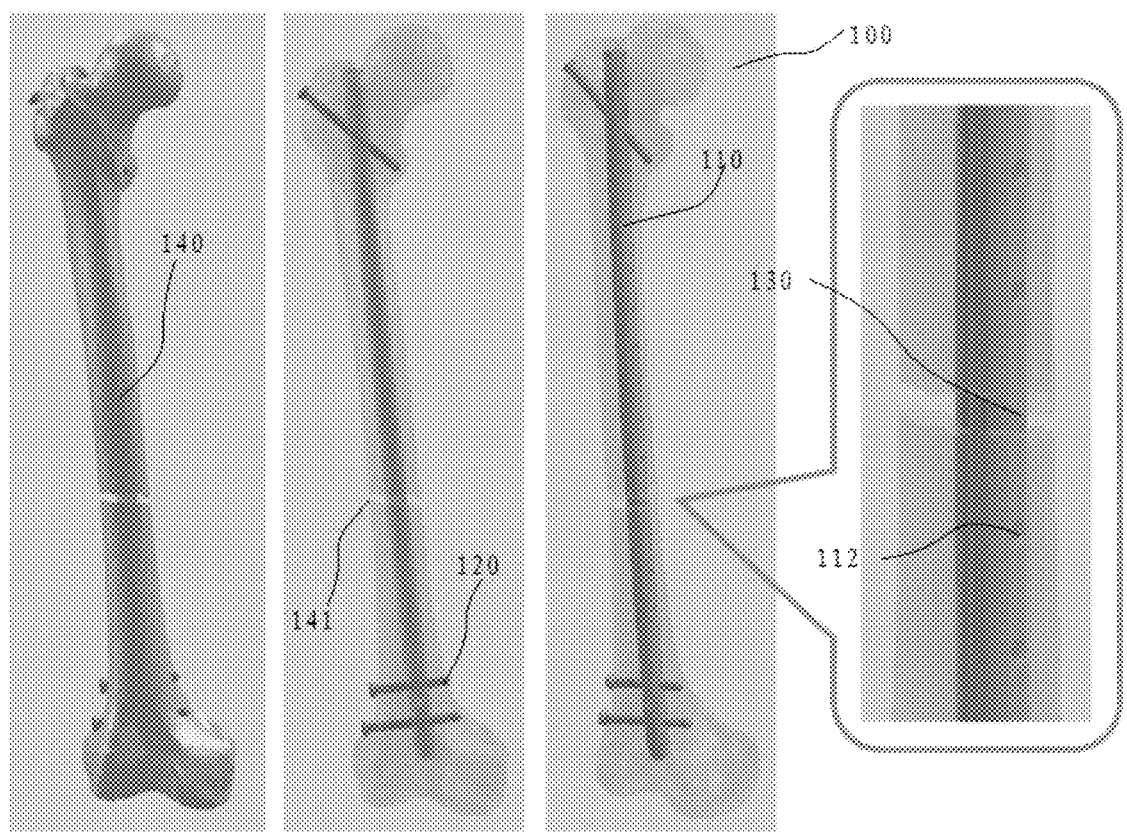
FIG. 1 shows a schematic perspective view and a partially enlarged view of a hybrid implant system according to an implementation of the present disclosure.

The present disclosure will be further detailed by combining the drawings and embodiments. It will be appreciated that the specific embodiments described herein are only for explaining relevant inventions, not for defining such inventions. It will also be noted that the drawings, for the sake of description, only illustrate the parts associated with the relevant inventions.

It will be appreciated that although terms such as first and second may be used herein to describe various elements, parts, assemblies or sections, these parts, elements, assemblies or sections should not be limited by these terms. These terms are only used to distinguish one element, part, assembly or section from a different element, part, assembly or section. Therefore, the first element, first part, first assembly or first section discussed below may be referred to as a second element, second part, second assembly or second section without departing from the teachings of the present disclosure.

For ease of description, terms for relative space positions such as "under . . . ", "below . . . ", "under", "above . . . ", "upper", "upper end" or "lower end" may be used herein to describe the relationship between one part or feature and a different part (different multiple parts) or a different feature (different multiple features) as shown in the figures. It will be appreciated that, in addition to the orientation depicted in the figures, the terms for relative space positions are intended to encompass different orientations of a device in use or in operation. For example, if a device in a figure is turned over, an element described as "below" or "beneath" a different element or feature would then be oriented "above" the different element or feature. Therefore, the exemplary term "below . . . " may encompass two orientations "above . . . " and "below . . . ".

The wording used herein is for the purpose of describing particular implementations only, and is not intended to limit the present disclosure. Unless otherwise clearly indicated in the context, the wording, if used herein, does not have a feature of defining singular forms and is intended to comprise the plural forms as well. It should also be understood that the terms "comprise", "comprising", "have", "contain" and/or "containing", when used in the description, specify the presence of stated features, integers, steps, operations, elements and/or parts, but do not preclude the presence or addition of one or more other features, integers, steps, operations, elements, parts and/or groups thereof. For example, the term "and/or" as used herein comprises any and all combinations of one or more of the associated listed items. Expressions such as "at least one of . . . " as appearing behind a list of elements modify the entire list of elements and do not modify the individual elements in the list. In addition, when the implementations of the present disclosure are described, "may" means "one or more implementations of the present disclosure". In addition, the term "exemplary" is intended to refer to an example or to illustrate.

As used herein, the terms "substantial" "approximate" and similar terms are used as terms indicating similarity, not as terms indicating degree, and are intended to describe the inherent deviations of a measurement value or a calculation value that will be understood by those skilled in the art.

Unless otherwise defined, all terms (comprising technical and scientific terms) used herein have the same meanings as those commonly understood by those skilled in the art to which the present disclosure belongs. It will be further understood that terms, such as those defined in commonly used dictionaries, should be interpreted as having meanings consistent with the meanings thereof in the context of the relevant art and will not be interpreted in an idealized or overly formal sense, unless expressly so defined herein.

It should be noted that, the embodiments in the present disclosure and the features in such embodiments may be combined with each other in the case of no conflict. The present disclosure will be described in detail below with reference to the accompanying drawings and embodiments.

The present disclosure will be further described in combination with specific implementations.

FIG. 1 is a schematic perspective view and a partially enlarged drawing of a hybrid implant system according to an implementation of the present disclosure. For clearly displaying the details of the hybrid implant system 100, the bone in views other than the left view in FIG. 1 is shown as translucent. In the exemplary implementation as shown in FIG. 1, the hybrid implant system 100 may comprise an implant body 110, a locking part 120 and a healing assembly 130.

In the present exemplary implementation, the implant body 110 may be a long tubular part and may have holes (not shown) on both ends thereof. The locking part 120 may be used to attach the implant body 110 to a broken bone 140 through the holes. In the present implementation, the locking part 120 may, for example, be a screw commonly used in orthopedic fixation. The healing assembly 130 may be made from a material capable of healing the broken bone 140, wherein the implant body 110 has at least one window 112 on a side thereof. The at least one windows 112 is aligned with the broken location 141 of the broken bone 140. The healing assembly 130 is inserted into the window 112 in a self-locking manner towards an interior of the implant body 110. In addition, there is no window 112 for inserting the healing assembly 130 on a concave-convex side of the implant body 110 since the concave-convex side is a region with high stress. The diameters of the holes on the implant body 110 and the window 112 as well as the spacing between the holes and the window 112 may be optimized to match the characteristics of the broken bone 140.

In an alternative implementation of the present disclosure, the hybrid implant system 100 is actually an intramedullary nail system placed in a broken bone. However, it will be appreciated that the hybrid implant system 100 may be a different device suitable for osteopathic treatment.

In an alternative implementation according to the present disclosure, the healing assembly 130 may be made from a material promoting and enhancing bone healing. In an exemplary implementation of the present disclosure, the healing assembly 130 may be made from magnesium (Mg) or magnesium alloys. The elastic modulus and compressive yield strength of the magnesium may match well with those of a natural bone, while magnesium has a greater toughness than ceramic biomaterials such as hydroxyapatite. In addition, about 60% of total physiological magnesium is stored in the bone matrix. Besides, magnesium deficiency may lead to osteoporosis in human body, while supplementing magnesium is beneficial for a patient with osteoporosis. In this case, it is attractive to develop magnesium as a scaffold material for orthopedic implants, not only for fracture fixation but also for healing enhancement.

Figure 2:
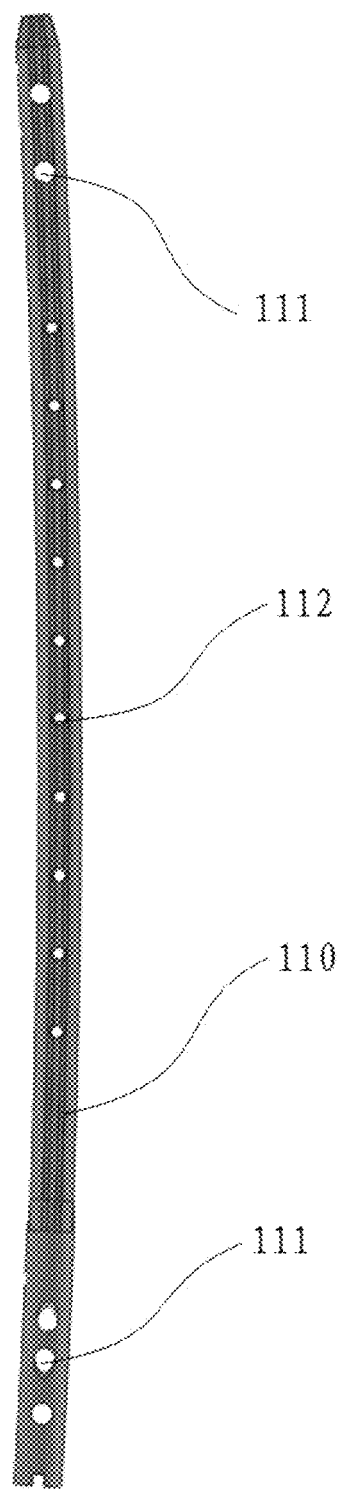
FIG. 2 shows a front view of an implant body of a hybrid implant system according to an implementation of the present disclosure.

FIG. 2 is a front view of an implant body 110 of a hybrid implant system 100 according to an implementation of the present disclosure. The implant body 110 may be a long tubular part and may have at least one holes 111 on both ends thereof. In addition, the implant body 110 has at least one window 112 on the side thereof. In the present implementation, the implant body 110 may be a hollow rod that is made from a metal and has a hollow cavity 115, and the curvature of the hollow rod may be designed to fit a broken bone. A suitable implant body 110 may be conductive to reducing the movement between an implant and a broken bone and reducing the recurrence of fracture.

In an alternative implementation according to the present disclosure, a surgeon may determine a broken location 141 with the help of a clinical image for the treatment of a long bone fracture. For a preoperative procedure, the implant body 110 will be aligned with the broken bone 140 and the healing assembly 130 will be positioned in the window 112 closest to the fracture location 141 of the broken bone 140, and then the mix system is inserted into the broken bone 140.

Figure 3:
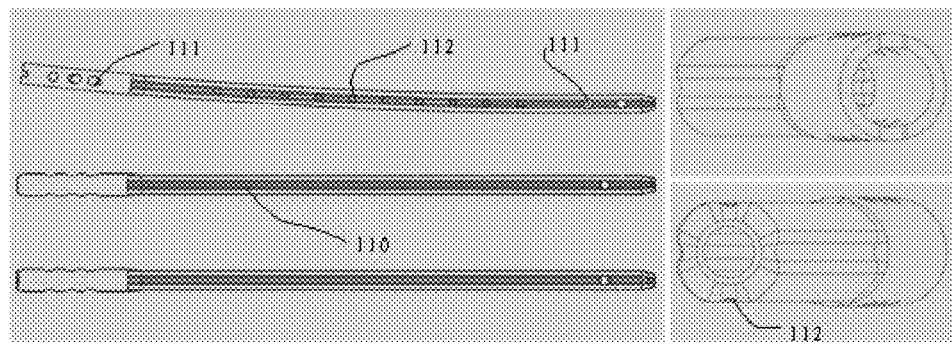
FIG. 3 shows various views of an implant body of a hybrid implant system according to an implementation of the present disclosure.

FIG. 3 is various views of an implant body 110 of a hybrid implant system 100 according to an implementation of the present disclosure. In the present implementation, one groove, for example, may be provided on each side of the implant body 110. Four grooves on the four sides of the body 110 may make an angle of about 90° with each other. This design can avoid full contact of nail to the bone marrow cavity, avoiding resistance of nail insertion into the bone marrow cavity. It can seen from the views, there may be two holes 111 for the locking part 120 on the distal end of the implant body 110. In addition, there may also be a plurality of holes for the same purpose at the proximal end of the implant body 110, for example, three holes 111 as shown in the figure. Two of the three holes are oblique so that the locking part 120 may be inserted at an angle to the cross-section of the implant body 110. Therefore, the locking part 120 may be inserted to as much as the bone contents and the implant body 110 is fixed to the bone, which may improve the stability of the implant body 110 inside the bone cavity. After finite element analysis (FEA), creating holes at the lateral sites would minimize the loss of mechanical properties at Anterior-Posterior (AP) direction as AP direction sustains more physiological loading in vivo. However, the location, orientation and alignment of windows are not limited to the pattern we showed in FIG. 3.

Figure 4:
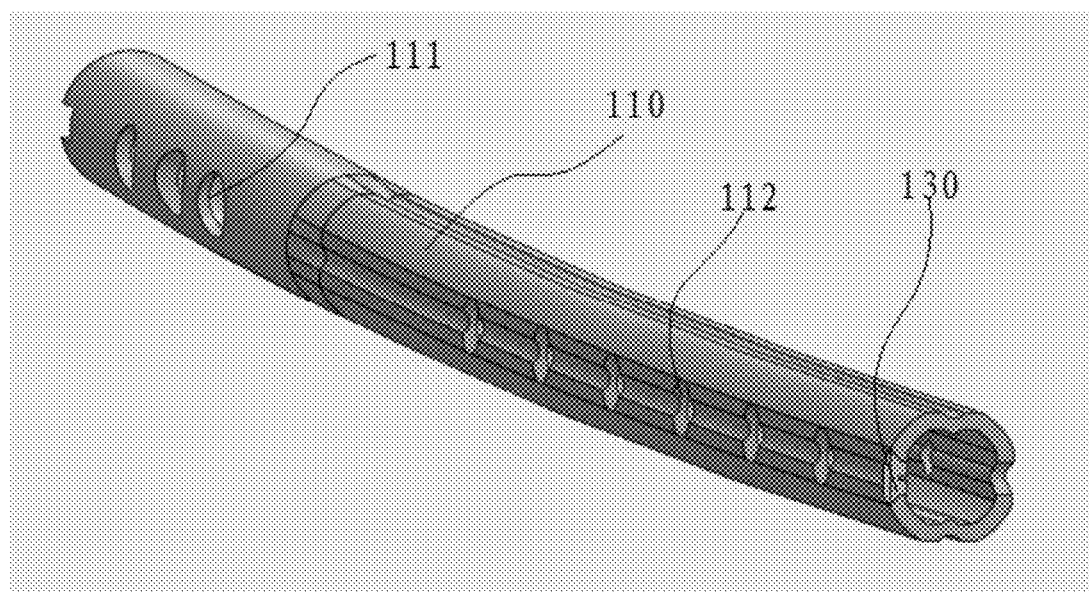
FIG. 4 shows a partial section perspective view of a combined implant body and healing assembly of a hybrid implant system according to an implementation of the present disclosure.
Figure 5:
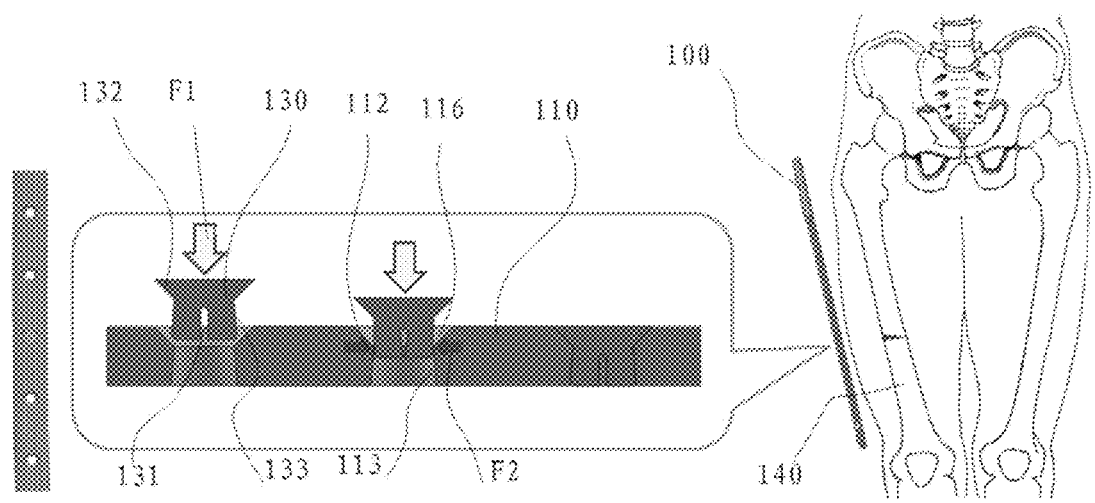
FIG. 5 shows a schematic diagram of a combination of a healing assembly of a hybrid implant system according to an implementation of the present disclosure.

FIG. 4 is a partial section space diagram of combined implant body 100 and healing assembly 130 of a hybrid implant system 100 according to an implementation of the present disclosure. FIG. 5 is a schematic section view of a combination of a healing assembly 130 of a hybrid implant system 100 according to an implementation of the present disclosure. As shown in FIG. 5, the healing assembly 130 may have a resilient groove 131. The healing assembly 130 may be inserted into the window 112 towards an interior of the implant body 110 and then the healing assembly 130 may be snapped into the window 112 by compressing the resilient groove 131.

The window 112 may comprise a first section 116 and a second section 113 in a direction from an outside to the inside along the side of the implant body 110. The first section 116 may have a inner diameter larger than a diameter of the second section 113 except for a combination of the two. In the present implementation, the first section 116 may be a partially tapered section that is opened outward, and the second section 113 may be a cylindrical cavity.

The healing assembly 130 may comprise a first holding section 132 and a second holding section 133, wherein a shape of the first holding section 132 may correspond to the first section 116, and a shape of the second holding section 133 may correspond to the second section 113, wherein the resilient groove 131 may be disposed in the second holding section 133.

In an alternative embodiment according to the present disclosure, the healing assembly 130 may be inserted directly into the window 112. During the insertion, the window 112 will squeeze the healing assembly 130 in a direction of an arrow F2, thus deforming the resilient groove 131, allowing the healing assembly 130 to be squeezed into the window 112. Once the healing assembly 130 is fully squeezed into the window 112, the healing assembly 130 will return to the original shape and will realize self-locking. The self-locking feature may prevent the healing assembly 130 from falling into the hollow cavity 115 of the implant body 110 when the healing assembly 130 is pushed into the window 112. As a result, the healing assembly 130 will be securely fixed in place. The healing assembly 130 will not fall off when the surgeon inserts the implant body 110 into the bone of a patient during surgery.

Figure 6:
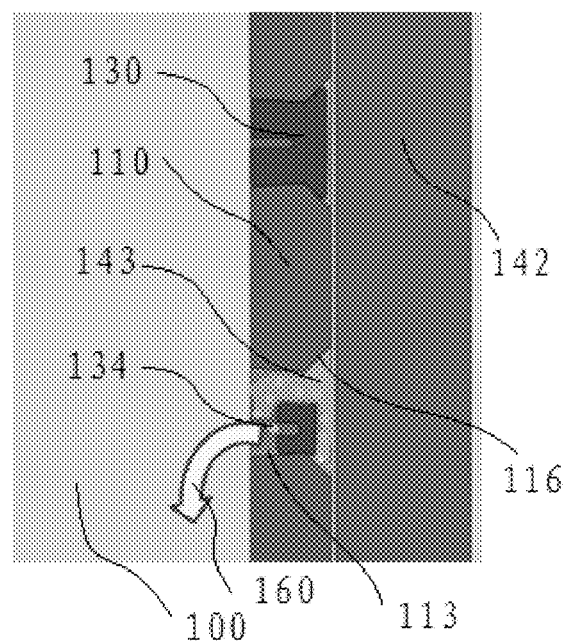
FIG. 6 shows a schematic diagram of a degradation process of a healing assembly of a hybrid implant system according to an implementation of the present disclosure.

FIG. 6 is a schematic diagram of a degradation process of a healing assembly 130 of a hybrid implant system 100 according to an implementation of the present disclosure, and the healing assembly 130 gradually degrades during implantation.

The upper part of FIG. 6 schematically illustrates a healing assembly 130 that is to start degrading, and the lower part of FIG. 6 illustrates a healing assembly 130 that has gradually degraded to fall off.

As shown in the upper part of FIG. 6, when the healing assembly 130 initially starts degrading, features of the first section 116 and the second section 113 of the window 112 as well as the first holding section 132 and the second holding section 133 of the healing assembly 130 may prevent the healing assembly 130 that starts degrading from falling into the hollow cavity 115 of the implant body 110. The healing assembly 130 is adjacent to a backbone wall 142 so that the healing assembly 130 is fully exposed to a fracture site.

As shown in the lower part of FIG. 6, when the healing assembly 130 has degraded, the shape thereof is no longer intact. The healing assembly 130 will lose the self-locking function thereof over time. A degradation product 134 (such as a magnesium ion) released by the healing assembly 130 pass through the holes and distributed to the surrounding bone tissue to promote the growth of a surrounding tissue 143, which in turn fills the window 112, and prevents the degrading healing assembly 130 from falling off.

If the healing assembly 130 still becomes loose and falls off from the window 112 in the fall off direction 160, the healing assembly 130 will fall into the hollow cavity 115 of the implant body 110 only.

Figure 7:
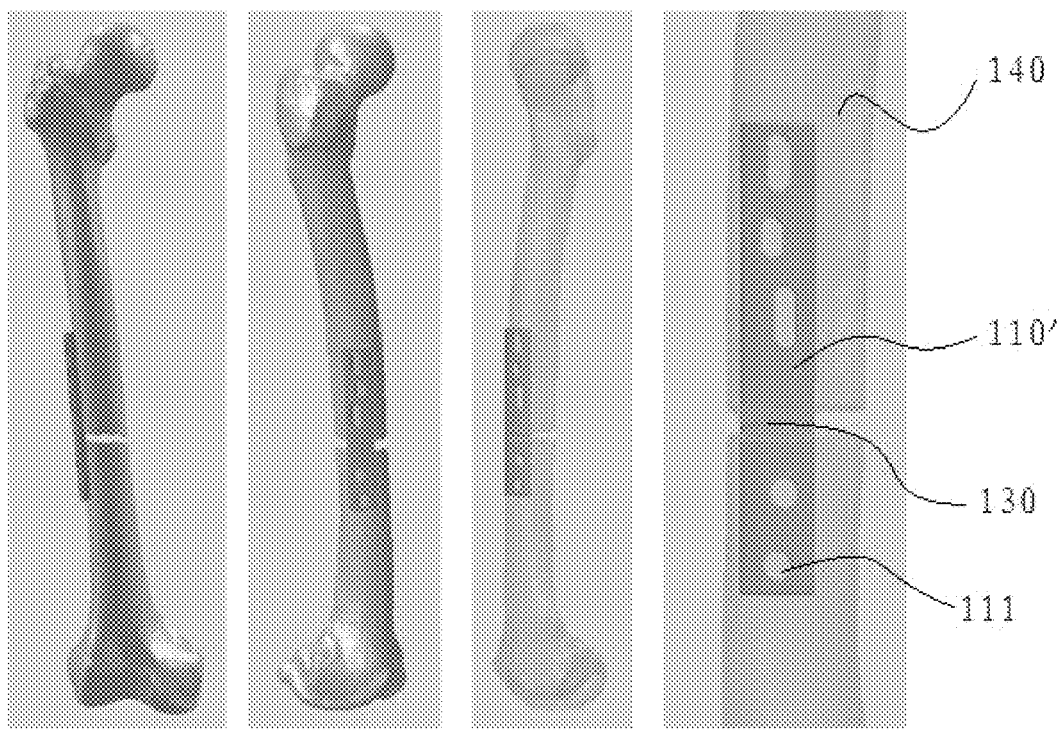
FIG. 7 shows a schematic space diagram and a partially enlarged view of a hybrid implant system according to another implementation of the present disclosure.
Figure 8:
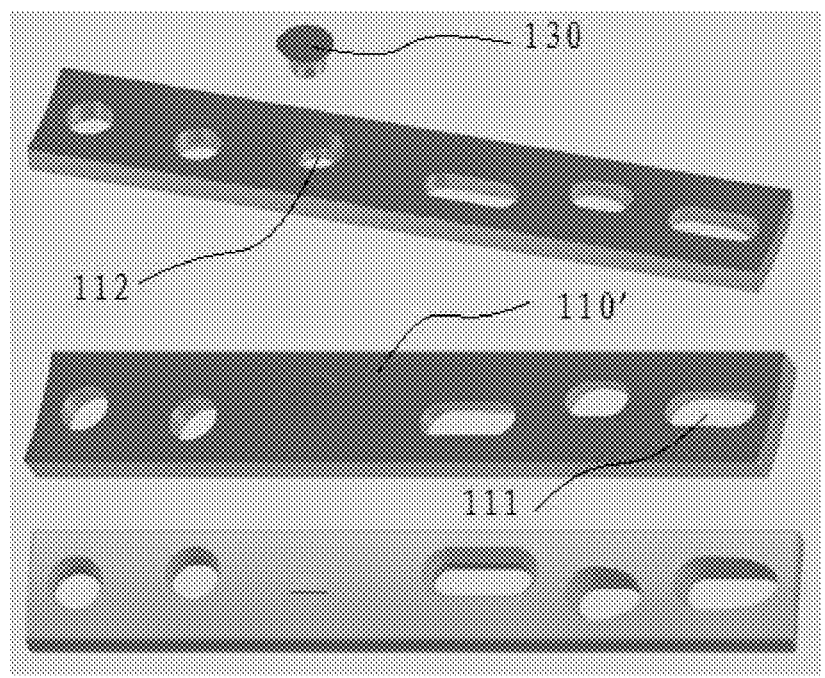
FIG. 8 shows a schematic diagram of a combination of an implant body and a healing assembly of a hybrid implant system according to an implementation of the present disclosure.
Figure 9:
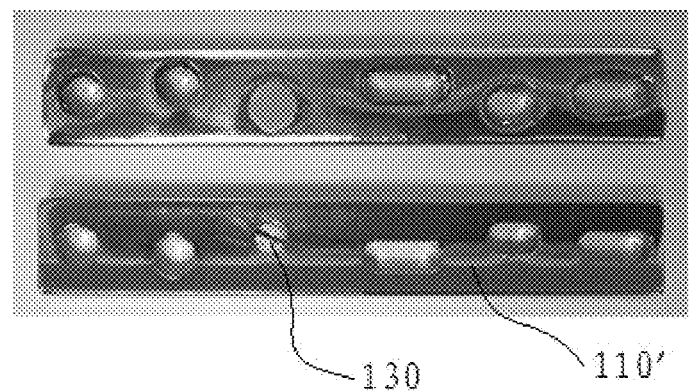
FIG. 9 shows a schematic perspective view of a hybrid implant system according to an implementation of the present disclosure.

FIG. 7 to FIG. 9 illustrate a hybrid implant system according to another implementation of the present disclosure. In contrast to the previously described implementations, an implant body 110' in the present embodiment may be attached to the outside of the broken bone 140 instead of being inserted into the broken bone 140. In the present implementation, the implant body 110' has a tubular outline. For clearly showing the details of the hybrid implant system 100, the bones in the views other than the left view in FIG. 7 are shown as translucent.

Figure 10:
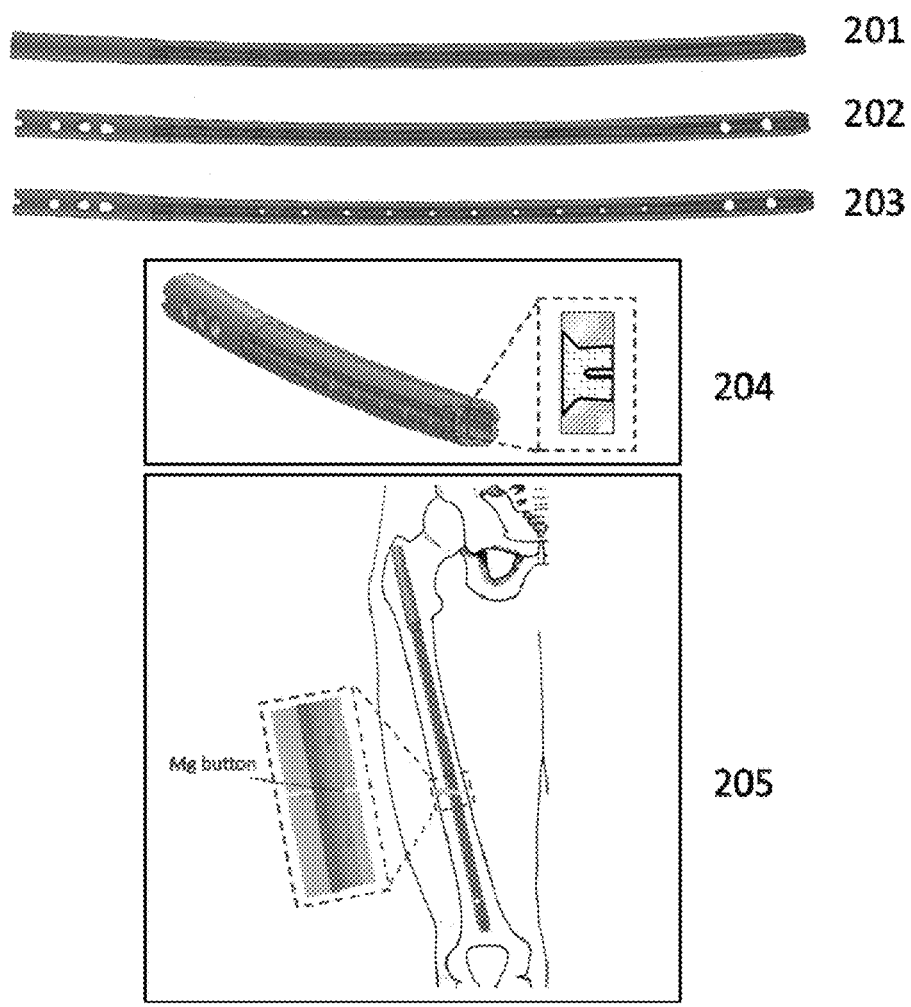
FIG. 10 is a sequence diagram of a method for manufacturing a hybrid implant system according to an implementation of the present disclosure.

FIG. 10 is a sequence diagram of a method for manufacturing a hybrid implant system according to an implementation of the present disclosure.

Referring to FIG. 10, the method 200 for manufacturing a hybrid implant system according to an implementation of the present disclosure starts from step 201. In step 201, forming holes on both ends of an implant body to attach the implant body to a broken bone through the holes.

Then in step 202, forming at least one window on the side of the implant body.

In step 203, manufacturing a healing assembly body with a material capable of promoting healing of the bone. In an alternative implementation according to the present disclosure, the healing assembly may be made from magnesium or magnesium alloys.

In step 204, forming a self-locking part in the healing assembly body.

In step 205, allowing at least one of the windows to align with the broken location of the bone, and inserting the healing assembly into the window in a self-locking manner through the self-locking part.

In an alternative implementation according to the present disclosure, the self-locking part has a resilient groove, the healing assembly is inserted into the window towards the interior of the implant body, and the healing assembly is snapped into the window by compressing the resilient groove.

According to an alternative implementation of the present disclosure, the step 202 may comprise: allowing the window to form a first section and a second section along the side of the body in sequence from the outside to the inside, the first section having a larger inner diameter than the second section. Step 203 may comprise: a first holding section with shape corresponding to the first section; and a second holding section with shape corresponding to the second section, the resilient groove being disposed in the second holding section.

Alternatively, the healing assembly gradually degrades during implantation, and the implant body is used for being inserted into the broken bone.

As mentioned above, the implant body is a hollow rod with a hollow cavity, and the healing assembly falls into the hollow rod only after fall off due to degradation.

Alternatively, the implant body may also be attached to the outer side of the broken bone. As mentioned above, the implant body may also have a tabular outline.

Figure 11:
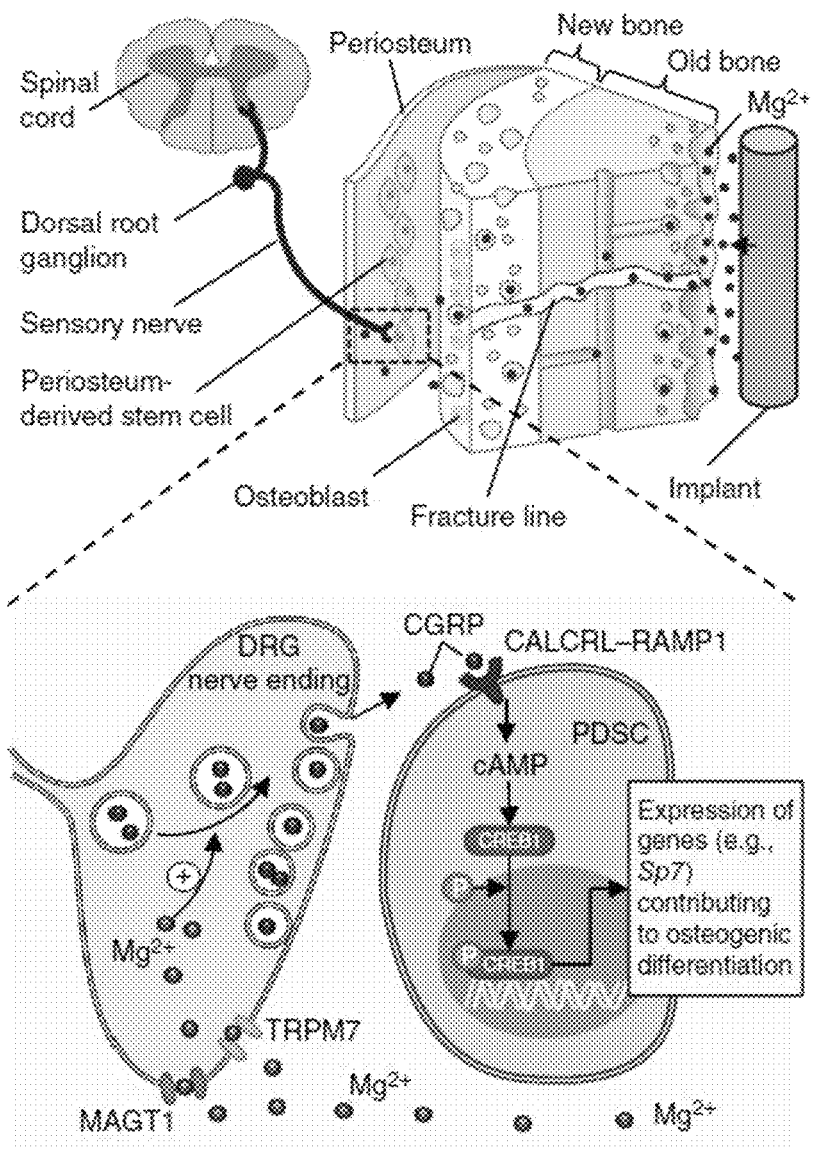
FIG. 11 shows mechanisms of osteoinductive effect of a degradation product release via upregulation of a bone forming neuro protein calcitonin gene-related peptide (CGRP) and its release to the fracture site.

FIG. 11 shows mechanisms of osteoinductive effect of a degradation product release via upregulation of a bone-forming neuro protein CGRP and its release towards the periosteum (bone fibrous membrane) to enhance fracture callus formation and its remodeling.

In this embodiment, the healing assembly 130 is made from magnesium, and thus the degradation product 134 is magnesium ion.

As illustrated in FIG. 11, magnesium ion stimulates sensory neurons to release neuro protein CGRP; CGRP promotes osteogenic differentiation of periosteum-derived stem cells (PDSCs) and the underlying molecular mechanisms of new bone formation. This magnesium ions releasing hybrid system significantly promotes fracture healing at weight bearing site through linking sensory neurons and PDSCs.

Figure 12:
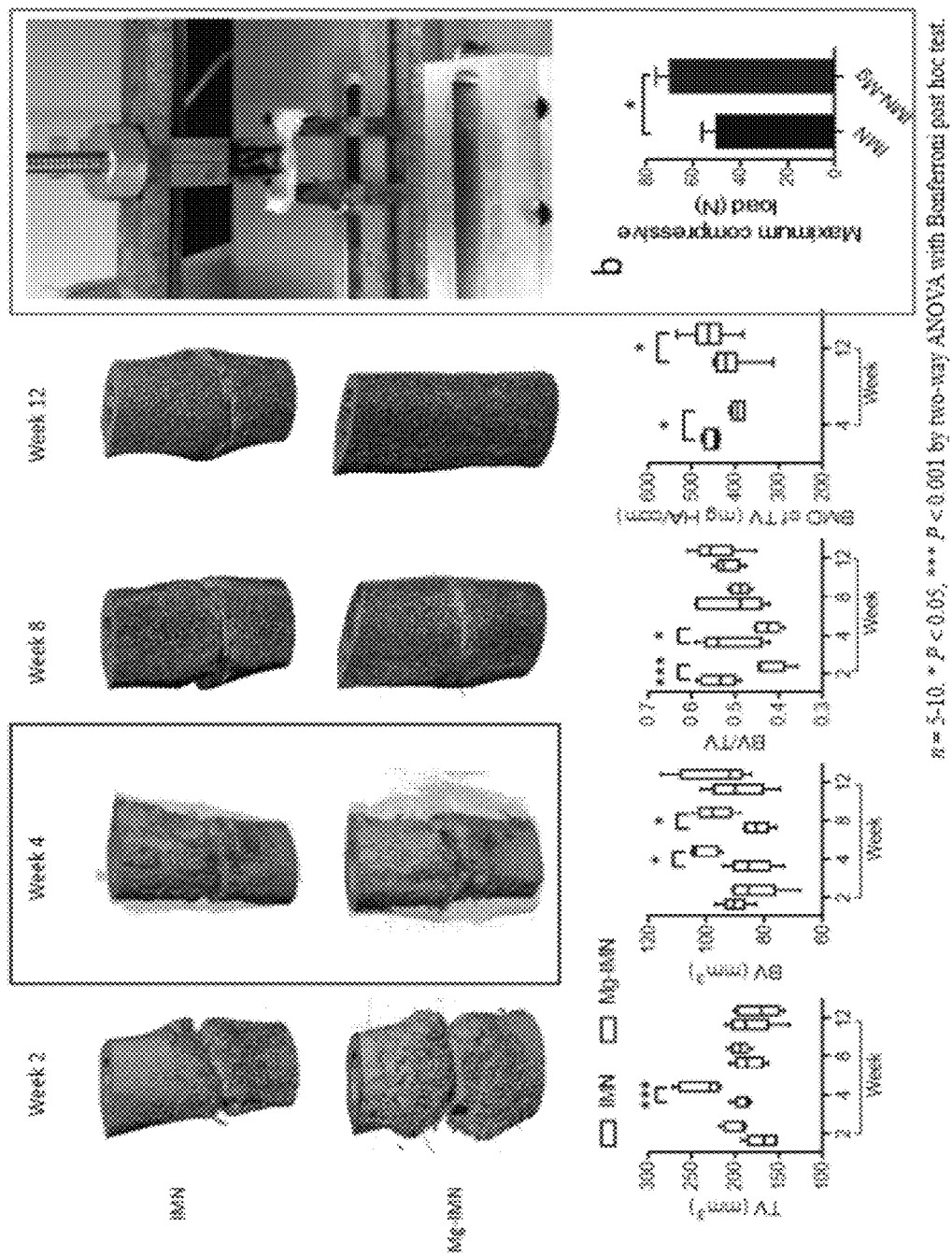
FIG. 12 illustrates the healing process with large fracture callus by using a Magnesium (Mg)-containing Intramedullary Nail (IM).

FIG. 11 illustrates how the magnesium ions releasing hybrid system promotes new bone formation through linking sensory neurons and PDSCs Four-point bending biomechanical test at week 12 that shows a significantly greater maximum compressive load (30% increase) of the femoral shafts in the hybrid system fixed group than in the conventional IMN group (refer to FIG. 12). The underlying biological mechanisms are related to Mg ions during Mg-implant degradation that diffuse across the bone toward the periosteum that is innervated by sensory neurons in dorsal root ganglion (DRG) and enriched with periosteum-derived stem cells (PDSCs) undergoing osteogenic differentiation into new bone. Then, the released Mg ions enter DRG neurons via Mg transporters or channels (i.e., MAGT1 and TRPM7) and promotes CGRP-vesicles accumulation and exocytosis. The DRG-released CGRP, in turn, activates the CGRP receptor (consisting of CALCRL and RAMP1) in PDSCs, which triggers phosphorylation of CREB1 via cAMP and promotes the expression of genes contributing to osteogenic differentiation.

According to an example of the present disclosure, in the hybrid system, one more feature/function is added to the conventional IM nailing system for achieving fracture healing enhancement effect, including facilitating bone healing, promoting bone formation, and increasing bone mechanical strength, etc. Therefore, in order to achieve this healing enhancement effect, windows are created on the IM nail and designed self-locking Mg plug to incorporate Mg (potentially all biologically safe healing enhancement biodegradable metals) with the IM nail. The concept of the hybrid system design can be also applied to other fracture fixation devices, such as locking and compression plates.

According to this example, Mg-based screws can be successfully applied for fixing bone fractures occurred at non-weight bearing sites in clinics. For example, a Mg-based MgYREZr screw is fabricated for hallux valgus surgery and CE mark approval can be obtained for clinical application, and Mg-5 wt % Ca-1 wt % Zn screw can be used to fix bone fractures at distal radius of the wrists in patients. A highly pure Mg screw (purity, 99.99%) can be applied to fix the vascularized bone graft to treat osteonecrosis of the femoral head. However, it is failed to fix femoral fracture (weight-bearing site) using Mg-based implants, owing to the rapid degradation at the initial phase which leads to impaired strength of the implant. Then, in order to make good use of the beneficial effect of Mg (i.e. enhancing bone formation), but avoid its weakness, a hybrid Mg-containing intramedullary nail is designed and assembled by inserting pure pin made of pure Mg pin into hollow nail with drilled holes (serving as vents for magnesium release). The efficacy of the hybrid intramedullary nail is firstly tested in the fixation of mid-shaft femoral fracture in osteoporotic rats. This hybrid system may significantly enlarge callus formation at early healing stage, whereas facilitating callus remodeling at late healing stage, and attributing to the magnesium-stimulated secretion of CGRP from dorsal root ganglion. The molecular and cellular mechanisms behind the biological effects of magnesium are identified at the first time by the inventors. The enhanced (30% increase vs conventional IMN) biomechanical strength of the healed bone is obtained, which is of defined great clinical importance.

FIG. 12 illustrates the healing process with large fracture callus by using a Mg containing Intramedullary Nail (IM). As shown in FIG. 12, the Mg containing Intramedullary Nail (IM) accelerates healing process with large fracture callus at week 4 post-implantation that enhances bone healing with significantly improved mechanical strength at later stage of healing.

Although the examples of the present disclosure have been described, those skilled in the art may make various modifications or changes to these examples on the basis of the known basic inventive concepts. It is intended that the appended claims are considered to comprise the examples and all modifications or changes that fall within the scope of the present disclosure.

It will be apparent for those skilled in the art to make various modifications or changes to the present disclosure without departing from the spirit or scope of the present disclosure. Therefore, these modifications or changes should also fall within the scope of the present disclosure if they belong to the scope of claims and an equivalent technology.

What is claimed is:

1. A hybrid implant system for fixing and repairing orthopedic fracture, comprising:
   an implant body, having holes on both ends; and
   a locking part, configured for attaching the implant body to a broken bone through the holes;
   a healing assembly made from a material promoting healing of the bone, the implant body having at least one window on a side, the at least one window aligned with a broken location of the bone, and the healing assembly inserted into the window in a self-locking manner towards an interior of the implant body, wherein the healing assembly has a resilient groove, the healing assembly is inserted into the window towards the interior of the implant body, and the healing assembly is snapped into the window by compressing the resilient groove.

2. The hybrid implant system according to claim 1, wherein the healing assembly is made from biodegradable magnesium or magnesium alloys.

3. The hybrid implant system according to claim 1, wherein the window comprises a first section and a second section on the side of the body in a direction from an outside to the inside, the first section having a diameter larger than a diameter of the second section;
   the healing assembly comprises:
   a first holding section having a shape corresponding to the first section; and
   a second holding section having a shape corresponding to the second section, the resilient groove being disposed in the second holding section.

4. The hybrid implant system according to claim 1, wherein the healing assembly gradually degrades during implantation.

5. The hybrid implant system according to claim 1, wherein the implant body is used for insertion into the broken bone.

6. The hybrid implant system according to claim 5, wherein the implant body is a hollow rod with a hollow cavity, and the healing assembly falls into the hollow cavity of the hollow rod only after falling off due to degradation.

7. The hybrid implant system according to claim 1, wherein the implant body is attached to an outer side of the broken bone.

8. The hybrid implant system according to claim 7, wherein the implant body has a plate shape.

9. A method for manufacturing a hybrid implant system, the method comprising:
forming holes on both ends of an implant body to attach the implant body to a broken bone through the holes;
forming at least one window on a side of the implant body;
manufacturing a healing assembly body with a material promoting healing of the bone; and
forming a self-locking part in the healing assembly body,
wherein, at least one window is aligned with a broken location of the bone, and the healing assembly is inserted into the window in a self-locking manner through the self-locking part, wherein the healing assembly has a resilient groove, the healing assembly is inserted into the window towards the interior of the implant body, and the healing assembly is snapped into the window by compressing the resilient groove.

10. The method for manufacturing a hybrid implant system according to claim 9, wherein the healing assembly is made from biodegradable magnesium or magnesium alloys.

11. The method for manufacturing a hybrid implant system according to claim 9, wherein forming at least one window on a side of the implant body comprises:
allowing the window to form a first section and a second section on the side of the body in a direction from an outside to the inside, the first section having a inner diameter larger than a diameter of the second section;
the healing assembly body manufactured with the material promoting healing of the bone comprising:
a first holding section having a shape corresponding to the first section; and
a second holding section having a shape corresponding to the second section,
the resilient groove being disposed in the second holding section.

12. The method for manufacturing a hybrid implant system according to claim 9, wherein the healing assembly gradually degrades during implantation.

13. The method for manufacturing a hybrid implant system according to claim 9, wherein the implant body is used for insertion into the broken bone.

14. The method for manufacturing a hybrid implant system according to claim 13, wherein the implant body is a hollow rod with a hollow cavity, and the healing assembly falls into the hollow rod only after falling off due to degradation.

15. The method for manufacturing a hybrid implant system according to claim 9, wherein the implant body is attached to an outer side of the broken bone.

16. The method for manufacturing a hybrid implant system according to claim 15, wherein the implant body has a plate shape.

* * * * *